(12) United States Patent
Mercier et al.

(10) Patent No.: US 8,939,158 B2
(45) Date of Patent: Jan. 27, 2015

(54) AGENTS, COMPOSITIONS AND DEVICES FOR TEMPORARY COLORING LOCAL HAIR AREAS

(75) Inventors: Michel Mercier, Hetzliya (IL); Shula Recanati, Tel Aviv (IL)

(73) Assignee: S.O.S. Color Ltd., Tel Aviv (IL)

( * ) Notice: Subject to any disclaimer, the term of this patent is extended or adjusted under 35 U.S.C. 154(b) by 0 days.

(21) Appl. No.: 12/817,524

(22) Filed: Jun. 17, 2010

(65) Prior Publication Data
US 2011/0005538 A1 Jan. 13, 2011

Related U.S. Application Data

(63) Continuation of application No. PCT/IL2008/001630, filed on Dec. 17, 2008.

(60) Provisional application No. 61/006,068, filed on Dec. 17, 2007.

(51) Int. Cl.
| | |
|---|---|
| A45D 24/22 | (2006.01) |
| A45D 34/04 | (2006.01) |
| A61K 8/72 | (2006.01) |
| A45D 19/02 | (2006.01) |
| A61K 8/19 | (2006.01) |
| A61K 8/60 | (2006.01) |
| A61Q 5/06 | (2006.01) |
| A45D 19/00 | (2006.01) |

(52) U.S. Cl.
CPC . *A61K 8/72* (2013.01); *A45D 19/02* (2013.01); *A45D 24/22* (2013.01); *A45D 34/04* (2013.01); *A61K 8/19* (2013.01); *A61K 8/602* (2013.01); *A61Q 5/065* (2013.01); *A45D 34/042* (2013.01); *A45D 2019/0083* (2013.01); *A45D 2200/057* (2013.01)

USPC .......................................... 132/112; 132/116

(58) Field of Classification Search
USPC .......... 132/112–116, 160; 401/190, 290, 272, 401/17, 25–27; 222/402.13, 402.15
See application file for complete search history.

(56) References Cited

U.S. PATENT DOCUMENTS

| | | | |
|---|---|---|---|
| 2,849,009 A | 8/1958 | Heinrich et al. | |
| 3,302,235 A * | 2/1967 | Gerber | 401/190 |
| 3,550,857 A * | 12/1970 | Ahlberg | 239/288 |

(Continued)

FOREIGN PATENT DOCUMENTS

| | | |
|---|---|---|
| DE | 29911802.9 | 11/2000 |
| DE | 10218502 | 10/2002 |

(Continued)

OTHER PUBLICATIONS

Machine generated translation of German patent application No. DE 10218502 A1, text extracted from PDF with "PDF OCR" and translated by google translate. Original German patent reference published Oct. 31, 2002.

(Continued)

*Primary Examiner* — Robyn Doan
(74) *Attorney, Agent, or Firm* — Marc Van Dyke; 4th Dimension IP

(57) ABSTRACT

Hair-coloring applicators comprising a shield to protect the scalp, polymers of tannic acid having iron ions bound thereto, hair-coloring compositions comprising same and/or melanoidin, and novel alcohol-free carriers, are disclosed, as well uses thereof for coloring hair.

24 Claims, 4 Drawing Sheets

(56) References Cited

U.S. PATENT DOCUMENTS

| | | | | |
|---|---|---|---|---|
| 3,636,963 | A | * | 1/1972 | Olson ............................ 132/112 |
| 3,854,489 | A | | 12/1974 | Doyle et al. |
| 3,964,501 | A | * | 6/1976 | Matchett ...................... 132/112 |
| 4,057,901 | A | | 11/1977 | Bloem |
| 4,068,782 | A | * | 1/1978 | Van der Heijden ...... 222/402.13 |
| 4,533,273 | A | * | 8/1985 | Obata et al. ................... 401/190 |
| 4,805,839 | A | * | 2/1989 | Malek ........................... 239/337 |
| 5,070,819 | A | * | 12/1991 | Helmstetter .................. 119/604 |
| 5,555,899 | A | | 9/1996 | Foreman |
| 5,772,077 | A | * | 6/1998 | Tafur ............................ 222/192 |
| D399,602 | S | | 10/1998 | Ratnam |
| D401,380 | S | | 11/1998 | Steen et al. |
| 5,842,905 | A | * | 12/1998 | Lee et al. ....................... 446/296 |
| 5,848,598 | A | * | 12/1998 | Walz et al. .................... 132/112 |
| D406,763 | S | * | 3/1999 | Watkins et al. ................. D9/448 |
| 5,913,314 | A | * | 6/1999 | Garrett .......................... 132/112 |
| 6,000,405 | A | * | 12/1999 | De Laforcade ............... 132/116 |
| 6,112,751 | A | | 9/2000 | Bennett |
| 6,286,518 | B1 | | 9/2001 | Laporte |
| D461,280 | S | | 8/2002 | Swaner et al. |
| D462,808 | S | | 9/2002 | Swaner et al. |
| 6,637,440 | B2 | * | 10/2003 | de Laforcade ............... 132/112 |
| 7,628,159 | B2 | * | 12/2009 | De Laforcade ............... 132/112 |
| D643,725 | S | | 8/2011 | Tiram |
| 2001/0029960 | A1 | | 10/2001 | Asano |
| 2004/0221862 | A1 | | 11/2004 | De Laforcade |
| 2006/0243293 | A1 | | 11/2006 | Lanne |
| 2008/0060665 | A1 | * | 3/2008 | Umeno et al. ................ 132/112 |

FOREIGN PATENT DOCUMENTS

| | | |
|---|---|---|
| DE | 20114390 | 1/2003 |
| EP | 0943260 | 9/1999 |
| EP | 1769697 | 4/2007 |
| FR | 2799621 | 4/2001 |
| JP | 59-190101 | 12/1984 |
| JP | 3-7302 | 1/1991 |
| JP | 3-111207 | 11/1991 |
| JP | 8117012 | 5/1996 |
| JP | 8168409 | 7/1996 |
| JP | 8214936 | 8/1996 |
| JP | 9002554 | 1/1997 |
| JP | 2003230426 | 8/2003 |
| JP | 2004154459 | 6/2004 |
| JP | 2004155484 | 6/2004 |
| JP | 2007297298 A * | 11/2007 |
| JP | 2008237693 | 10/2008 |
| JP | 2009106655 | 5/2009 |
| WO | WO9604814 | 2/1996 |
| WO | WO2005060786 | 7/2005 |

OTHER PUBLICATIONS

Machine generated translation of German patent application No. DE 20114390 U1, text extracted from PDF with "PDF OCR" and translated by google translate. Original German patent reference published Jan. 16, 2003.

Machine generated translation of German patent application No. DE 29911802 U1, text extracted from PDF with "PDF OCR" and translated by google translate. Original German patent reference published Nov. 16, 2000.

Machine generated translation for Japanese patent application No. JP 8117012. Japanese document published May 14, 1996.

Machine generated translation for Japanese patent application No. JP 8168409. Japanese document published Jul. 2, 1996.

Machine generated translation for Japanese patent application No. JP 9002554. Japanese document published Jan. 7, 1997.

PCT Search report of PCT/IB2011/052767, mailed Feb. 22, 2012.

PCT Search opinion of PCT/IB2011/052767, Feb. 22, 2012.

List of References for U.S. Appl. No. 29/397,379, filed Jul. 14, 2011.

Office Action of rejection from the Japanese patent office, dated Oct. 10, 2013, for JP patent application No. 2010-539045, Titled "Agents, Compositions and Devices".

Translation of Japanese patent publication No. H03-7302 (Application No. H01-65499). Japanese application originally published Nov. 14, 1991 Cited by Office Action of Oct. 10, 2013 for JP patent application No. 2010-539045.

Translation of Japanese patent publication No. H03-111207 (Application No. H02-19809). Japanese application originally published Jan. 14, 1991 Cited by Office Action of Oct. 10, 2013 for JP patent application No. 2010-539045.

PCT search report/search opinion/patentability opinion for PCT/IL2008/001630 (parent case of the present application)—Nov. 2009 through Jun. 2010.

Machine-generated translation of JP2009106655 (May 2009).

Machine-generated translation of JP2008237693 (Oct. 2008).

Machine-generated translation of JP2004154459 (Jun. 2004).

Machine-generated translation of JP2003230426 (Aug. 2003).

Machine-generated translation of JP2004155484 (Jun. 2004).

* cited by examiner

AGENTS, COMPOSITIONS AND DEVICES FOR TEMPORARY COLORING LOCAL HAIR AREAS

CROSS-REFERENCE TO RELATED APPLICATIONS

This patent application is a continuation of PCT/IL2008/001630 filed on Dec. 17, 2008 and published as WO/2009/078017, and claims priority to U.S. Provisional Application 61/006,068 filed on Dec. 17, 2007, which are all hereby incorporated in their entirety by reference.

FIELD AND BACKGROUND OF THE INVENTION

The invention, in some embodiments thereof, relates to the temporary coloring of graying hair, and, more particularly, to agents, formulations, compositions and devices which are useful for temporary shading off local areas of gray or white hair rapidly and simply.

Hair dyes are commonly used to hide the gray and white hairs typically caused by aging, as well as to alter other hair colors to suit personal taste. Hair colorants may be broadly classified into several types, although colorants of different types may be combined, and some colorants may not clearly belong to any one type [Anderson, *J. Soc. Dyers Colourists*, 116:193-196 (2000); Zviak and Millequant, [Zviak, Charles; Millequant, Jean. Editor(s): Bouillon, Claude; Wilkinson, John. Science of Hair Care (2nd Edition) (2005), 251-275. Publisher: CRC Press LLC, Boca Raton, Fla].

Permanent colorants are usually formed by mixing small aromatic precursors with an oxidizing agent, typically hydrogen peroxide. Following oxidation, the precursors covalently react with each other to form a dye. The small precursor molecules can diffuse into the hair more effectively than the larger dye molecule can diffuse out. An alkalizing agent, typically ammonia, is also added in order to cause swelling of the hairs, which allows maximum penetration of the precursors into the hair. In addition, the peroxide bleaches the original hair color, thereby allowing the color of the dye to completely replace the original hair color. Permanent colorants are quite popular, but they suffer the drawbacks of the complexity of correctly mixing and applying the precursors, and the use of potentially harmful reagents. Thus, permanent colorants are normally applied by professional hair stylists. In addition, even permanent coloring cannot hide the original hair color that inevitably reappears with the new growth of hair.

Demi-permanent colorants are similar to permanent colorants, but use lower concentrations of peroxide, and an alkalizing agent that is less effective than ammonia, but has a less unpleasant odor. Demi-permanent colorants are therefore less effective at penetrating the hair and bleaching the original hair color, and cannot be used to effectively color predominantly gray or white hair. However, the relative gentleness of such colorants makes them desirable when less effective coloring is sufficient, such as when gray or white hairs constitute a minority of hairs.

Semi-permanent colorants typically comprise molecules, such as nitrophenylenediamines and nitroaminophenols, which are small enough to diffuse into the hairs. Such colorants do not require additional reagents and are therefore easy to use, but they are less effective than permanent dyes, fade relatively quickly following several shampooings, and cannot bleach the original hair color.

Temporary colorants typically do not penetrate the hairs, and therefore are capable of only moderate changes in hair color. They are also removed by the first shampooing, and are therefore appropriate for individual occasions, and to make slight alterations to hair color, such as hiding gray or white new growth, until a more permanent colorant is applied. Because temporary colorants need not comprise small molecules capable of penetrating the hair, a wide variety of compounds may be used, which facilitates convenience. For instance, one may select dyes that have no risk of inducing an allergic reaction, which is not possible with more permanent colorants. There is also a large number of shades to choose from.

The ideal characteristics of a temporary hair colorant depend on the exact use of the colorant. Typically, however, it is important that the colorant be easily removable by shampoo, but not by rain, perspiration or friction from clothing or pillowcases. It is also desirable that the colorant have a sufficiently high affinity to hair, and to color hair evenly.

Temporary hair colorants have been used as ingredients in shampoos and conditioners, shading strengtheners, colored hair sprays and mascaras, aimed to be applied to the entire head of hair or as hair streaks. To provide even and stable coloring there are often several families of dyes used within a single formula. The charge of the dyes can be negative or positive to provide low or high affinity to the hair shaft, as dyes with positive charge (basic dyes) have a higher affinity to the hair.

Common temporary hair colorants include azo derivatives, basic triphenylmethane dyes such as methyl violet, azine derivatives such as safranine, and indoamines and indophenols [Zviak and Millequant, supra (2005)]. Colored polymers have been used, as well as artificial melanin.

Polymer colorants with a strong affinity to hair are often semi-permanent or permanent colorants. Examples of polymers with a strong affinity to hair which are semi-permanent colorants are disclosed in U.S. Pat. Nos. 4,182,612, 5,702,712 and 5,827,330.

A polymeric temporary colorant thereafter must have at most a moderate affinity to hair, and more desirable, a low affinity to hair. Examples of polymers suitable for temporary coloring of hair are disclosed, for example in U.S. Pat. Nos. 5,737,907 and 5,891,199.

Tannic acid, or gallic acid produced by hydrolysis of tannic acid, has for centuries been combined with ferrous ions to produce iron gall ink. After writing with the pale ink, the ferrous ions are oxidized by atmospheric oxygen to ferric ions, which react with the tannic acid to produce a dark violet-black organometallic polymer that can permanently bind to proteins, such as those in parchment. Iron gall ink is rarely used today, because paper does not comprise protein, and excess iron atoms are highly corrosive, damaging both paper and pens.

A similar process has been used to permanently or semi-permanently dye hair with a dye that binds the protein of hair. For example, EP Patent No. 327,345 discloses a kit which comprises a shampoo comprising ferrous ion for washing hair, and a solution comprising tannic acid which is applied to the hair after shampooing in order to create a semi-permanent black dye. Such a kit is inadequate for use as a temporary colorant because the colorant is semi-permanent, and because the use of two solutions (a tannic acid solution and a ferrous ion solution) is too lengthy and complex to appeal to consumers. Moreover, the kit disclosed therein must be used more than once in order to achieve full coloration.

Japanese Patent No. 2,014,324 and U.S. Pat. No. 4,946,472 disclose hair colorants comprising ferric ion and tannic acid in a single formulation. The colorants used in the taught formulations, however, are not temporary.

Chinese Patent Application No. 1990-104,017, Japanese Patent Nos. 3,014,160 and 48,031,902 and Japanese Patent Application Nos. 2002-47,287, 1993-312,065, 1988-292,113 and 1984-65,068 disclose permanent or semi-permanent hair colorants comprising ferrous iron and tannic acid in a single formulation. Based on the art of iron-tannic acid colorants, it is believed that ferrous ion undergoes oxidation to ferric ion (e.g. by exposure to air) before reacting with tannic acid to produce a colored polymeric iron tannate. Oxidation of ferrous ions in a hair colorant that has been applied to the hair results in the formation of an iron tannate polymer strongly bound to the hair, making the colorant non-temporary. These patents and patent applications are silent with respect to compositions that comprise tannic acid and ferric iron ions, let alone compositions that are devoid of unbound ferric ions.

Japanese Patent Nos. 61,055,483, 130,823, 94,800 and 93,052 and Japanese Patent Application Nos. 2005-206,160, 2000-85,556, 1990-336,606, 1987-245,287, 1984-177,514 and 1972-81,137 disclose permanent or semi-permanent hair colorants comprising two formulations, one of which comprises iron ions, and the other comprising tannic acid. Mixture of the two solutions in hair allows the production of iron tannates in the hair, the iron tannates thereby becoming bound to the hair.

In addition to the inability of such formulations to serve as temporary colorants, iron-tannic acid hair colorants suffer from several general deficiencies. The dark black color does not appeal to many consumers. In addition, all of the abovementioned formulations comprise unbound iron ions. Unbound iron is corrosive, and ferrous ion in particular produces highly oxidizing free radicals by the Fenton reaction. Excess iron can damage hair and cause unsightly skin hyperpigmentation [Landsown, *Int. J. Cosmetic Sci.*, 23:129-137 (2001)].

Melanoidins are a family of brownish, colored compounds that result from the interaction between sugars and amino acids under moderate heat. Melanoidins are responsible for much of the browning and flavor of cooked foods, and hence are recognized as highly safe agents. However, melanoidins have not been disclosed as hair colorants heretofore.

It is advantageous for temporary hair colorants to comprise a formulation suitable for applying the colored compound(s) included therein to the hair with the desired ease and convenience. For example, the formulation may include solvents and/or surface active agents which allow the solubilization of the colored compound, and yet are fast drying formulation. It is also desirable in many cases for the formulation to include ingredients that prevent the temporary hair coloring from fading and/or rubbing off prematurely.

PCT Patent Application No. WO 94/10968 teaches an aqueous hair dye composition comprising solubilized melanin and a cationic material which binds the solubilized melanin to the hair via electrostatic interactions. The melanin is preferably solubilized by being oxidized with hydrogen peroxide, which is taught therein as imparting an ionic character to the melanin. The cationic material, such as a quaternium or polyquaternium compound, is taught therein as complexing the anionic melanin in a manner that increases the affinity of the melanin to the hair.

U.S. Pat. No. 6,506,374 teaches a hair coloring composition comprising alcohols to allow quick drying, and a polymer which prevents the color from rubbing off.

U.S. Pat. No. 5,821,240 teaches an aqueous hair coloring composition which includes a quaternary ammonium functional silane to prevent rubbing off.

Japanese Patent Application No. 1993-312,065 teaches a hair coloring composition comprising tannic acid, ferrous salts, and a silicone oil such as a silicone-polyether copolymer. Such silicone oils are non-volatile surface active agents useful in forming smooth films on hair.

As temporary hair colorants are desired for the potential ease and convenience of their use, it is particularly advantageous to have a quick and convenient technique for applying such colorants. Colorants in the form of pencils or wick-type applicators (e.g., U.S. Pat. No. 5,964,222) are frequently used to touch-up the hair along the hair line. Another technique involves combing into the hair a temporary hair colorant gel. In a further technique, hair colorant powder is applied by squeezing a bottle or by an aerosol container to dispense the powder, which is then worked into the hair line with the fingers.

However, none of these techniques is completely satisfactory, particularly when the subject wishes to touch-up the hair line in a quick and convenient manner, without staining or touching the skin.

SUMMARY OF THE INVENTION

According to one aspect of the embodiments of the present invention, there is provided a hair-coloring applicator comprising a container for containing a quantity of hair-coloring composition including an outlet at one end of the container through which the hair-coloring composition may be dispensed, and a shield projecting outwardly from one end of the container. The shield includes a plurality of closely spaced teeth having inner surfaces to be pressed against the subject's scalp with the root regions of the hairs passing through the spaces between the teeth, and outer surfaces to be exposed to the hair-coloring spray composition dispensed from the container such that the hair-coloring composition coats the root regions of the hairs passing through the spaces between the teeth, while the teeth substantially block the hair-coloring composition from reaching the subject's scalp. The abovementioned applicator is particularly useful for touching-up hair along a hairline of an individual.

As used herein, the phrase "touching-up" describes the coloring of hair in a quick and simple manner. This phrase further describes the coloring of local areas of hair, particularly local areas of gray or white hair such as the root region or parts thereof. The phrase "root region" describes the part of a hair closest to the scalp.

According to an embodiment of the present invention, the shield is carried by an attachment to the end of the container, and the container is an aerosol container for dispensing the hair-coloring composition in the form of a spray through a nozzle.

As used herein, the phrase "aerosol container" describes any container suitable for releasing a composition contained therein in the form of a spray. For example, the container should be capable of withstanding the internal pressure of a pressurized composition, and the nozzle should be configured so as to allow escaping pressurized composition to escape in the form of an aerosol.

In some embodiments, the abovementioned attachment includes an opening aligned with the nozzle.

According to an embodiment of the present invention, the abovementioned attachment further includes a push button controlling the dispensing of hair-coloring composition via the nozzle. In some embodiments, the abovementioned opening in the attachment that is aligned with the nozzle is located between the shield and the push button, such that the push button can be reached through the opening.

According to an embodiment of the present invention, the push button and the opening are located on an outer surface of the attachment, wherein the attachment slants towards the shield.

According to an embodiment of the present invention, the spaced teeth of the shield are parallel to the longitudinal axis of the container. Preferably, the teeth are arrayed in a generally linear array that is laterally spaced from the longitudinal axis of the container.

According an embodiment of the present invention, the teeth are less than 2 mm in width, thickness, and spacing.

According to an embodiment of the present invention, the teeth are tapered to a point at their outer tips.

According to an embodiment of the present invention, the applicator further comprises an outer housing enclosing the abovementioned container, the outer housing serving as a handle for gripping and manipulating the applicator. The outer housing may have any shape that is suitable for being held by hand.

According to an embodiment of the present invention, the outer housing and the container are both cylindrical.

According to another embodiment of the present invention, the container is cylindrical, and the outer housing is non-cylindrical.

According to an embodiment of the present invention, there is provided a hair coloring applicator comprising a container containing a quantity of hair coloring composition and including an outlet at one end of the container through which the hair coloring composition is dispensed and an attachment attached to the end of the container carrying the outlet, the attachment including a shield. The shield has a plurality of spaced teeth which pass between the subject's hairs to expose the root regions of the hairs passing through the teeth, while the teeth substantially block the hair coloring composition from passing through to the subject's scalp. Such an applicator is particularly useful for touching-up hair along a hairline of a subject.

According to some embodiments of the invention, the hair coloring composition comprises:

(i) at least one hair coloring agent selected from the group consisting of a first hair coloring agent which comprises a purified polymer of tannic acid having bound thereto iron ions, the purified polymer being substantially devoid of unbound iron ions, and a second hair coloring agent which comprises a condensation polymer of a reducing carbohydrate and an amino acid; and (ii) a suitable carrier.

According to some embodiments of the invention, the hair coloring composition comprises at least one hair coloring agent and a carrier which comprises:

(i) a hydrophobic volatile solvent, in a concentration that ranges from 20 to 60 weight percents;

(ii) water, in a concentration that ranges from 20 to 60 weight percents;

(iii) a glycol, in a concentration that ranges from 0.5 to 10 weight percents; and (iv) a surface active agent, in a concentration that ranges from 0.1 to 7.5 weight percents;

the formulation being substantially devoid of an alcohol.

According to some embodiments of the invention, the hair coloring composition comprises:

(a) at least one hair coloring agent selected from the group consisting of a first hair coloring agent which comprises a purified polymer of tannic acid having bound thereto iron ions, the purified polymer being substantially devoid of unbound iron ions, and a second hair coloring agent which comprises a condensation polymer of a reducing carbohydrate and an amino acid; and (b) a carrier which comprises:

(i) a hydrophobic volatile solvent, in a concentration that ranges from 20 to 60 weight percents;

(ii) water, in a concentration that ranges from 20 to 60 weight percents;

(iii) a glycol, in a concentration that ranges from 0.5 to 10 weight percents; and (iv) a surface active agent, in a concentration that ranges from 0.1 to 7.5 weight percents;

the carrier being substantially devoid of an alcohol.

According to an aspect of some embodiments of the present invention there is provided a hair coloring composition comprising at least one hair coloring agent and a carrier, the carrier comprising:

(i) a hydrophobic volatile solvent, in a concentration that ranges from 20 to 60 weight percents;

(ii) water, in a concentration that ranges from 20 to 60 weight percents;

(iii) a glycol, in a concentration that ranges from 0.5 to 10 weight percents; and (iv) a surface active agent, in a concentration that ranges from 0.1 to 7.5 weight percents;

the carrier being substantially devoid of an alcohol.

According to an aspect of some embodiments of the present invention there is provided a hair coloring composition comprising:

(i) at least one hair coloring agent selected from the group consisting of a first hair coloring agent which comprises a purified polymer of tannic acid having bound thereto iron ions, the purified polymer being substantially devoid of unbound iron ions, and a second hair coloring agent which comprises a condensation polymer of a reducing carbohydrate and an amino acid; and (ii) a suitable carrier.

According to an aspect of some embodiments of the present invention there is provided a hair coloring composition comprising:

(a) at least one hair coloring agent selected from the group consisting of a first hair coloring agent which comprises a purified polymer of tannic acid having bound thereto iron ions, the purified polymer being substantially devoid of unbound iron ions, and a second hair coloring agent which comprises a condensation polymer of a reducing carbohydrate and an amino acid; and (b) a carrier which comprises:

(i) a hydrophobic volatile solvent, in a concentration that ranges from 20 to 60 weight percents;

(ii) water, in a concentration that ranges from 20 to 60 weight percents;

(iii) a glycol, in a concentration that ranges from 0.5 to 10 weight percents; and (iv) a surface active agent, in a concentration that ranges from 0.1 to 7.5 weight percents;

the formulation being substantially devoid of an alcohol.

According to an aspect of some embodiments of the present invention there is provided a hair coloring agent comprising a purified polymer of tannic acid having bound thereto iron ions, the purified polymer being substantially devoid of unbound iron ions.

According to some embodiments of the invention, the iron ions comprise iron (III) ions.

According to some embodiments of the invention, the iron ions substantially consist of iron (III) ions.

According to some embodiments of the invention, the hair coloring agent is characterized by a black-violet color.

According to some embodiments of the invention, the purified polymer has an average molecular weight of at least 10 kDa.

According to some embodiments of the invention, the hair coloring agent is water-soluble.

According to some embodiments of the invention, there is provided a process of preparing the hair coloring agent, the process comprising:

reacting a tannic acid and an iron salt, to thereby obtain a polymer of tannic acid having iron ions bound thereto; and purifying the polymer, thereby obtaining the hair coloring agent.

According to some embodiments of the invention, the tannic acid and the iron salt are reacted in an aqueous solution.

According to some embodiments of the invention, the iron salt is a ferric salt.

According to some embodiments of the invention, the ferric salt is ferric ammonium citrate.

According to some embodiments of the invention, a concentration of the tannic acid in the aqueous solution ranges from 10 weight percents to 75 weight percents.

According to some embodiments of the invention, a weight ratio of iron ions of the iron salt and the tannic acid ranges from 1:5 to 1:500 by weight.

According to some embodiments of the invention, the purifying comprises gel exclusion chromatography.

According to some embodiments of the invention, the purifying comprises ultrafiltration.

According to some embodiments of the invention, the hair coloring agent is eluted by an aqueous solution.

According to some embodiments of the invention, the hair coloring agent is obtained by collecting at least one substantially colored fraction eluted by the aqueous solution.

According to some embodiments of the invention, there is provided a use of the hair coloring agent in the manufacture of a hair coloring composition.

According to some embodiments of the invention, there is provided a hair coloring composition comprising the hair coloring agent and a suitable carrier.

According to an aspect of some embodiments of the present invention there is provided a use of a composition-of-matter which comprises a condensation polymer of a reducing carbohydrate and an amino acid in the manufacture of a hair coloring composition.

According to an aspect of some embodiments of the present invention there is provided a hair coloring composition comprising of a composition-of-matter which comprises a condensation polymer of a reducing carbohydrate and an amino acid and a suitable carrier.

According to some embodiments of the invention, the condensation polymer is a water-soluble polymer.

According to some embodiments of the invention, the reducing carbohydrate is selected from the group consisting of a reducing sugar, a monosaccharide and a hexose.

According to some embodiments of the invention, the reducing carbohydrate is glucose.

According to some embodiments of the invention, the amino acid is glycine.

According to some embodiments of the invention, a weight ratio of the reducing carbohydrate and the amino acid in the condensation polymer ranges from 3:1 to 1:3.

According to some embodiments of the invention, the hair coloring composition is for coloring white or gray hair.

According to some embodiments of the invention, the hair coloring is temporary hair coloring.

According to some embodiments of the invention, the hair coloring composition is detergent-sensitive.

According to some embodiments of the invention, the hair coloring is useful for touching-up hair along a hairline of an individual.

According to some embodiments of the invention, the composition is in a form of a spray.

According to some embodiments of the invention, the composition is packaged in an applicator adapted for dispensing the composition onto hair, and identified for use in hair coloring.

According to some embodiments of the invention, the composition is identified for coloring white or gray hair.

According to some embodiments of the invention, the composition is identified for use in temporary hair coloring.

According to some embodiments of the invention, the composition is identified for touching-up hair along a hairline of an individual.

According to some embodiments of the invention, the applicator is selected from the group consisting of a wick-type applicator, a squeeze bottle, an aerosol container, a comb-type applicator, a drop dispenser and a pump-type applicator.

According to some embodiments of the invention, the carrier further comprises an emulsion stabilizer.

According to some embodiments of the invention, the emulsion stabilizer is a polymer.

According to some embodiments of the invention, the polymer is selected from the group consisting of acrylate/C10-30-alkyl acrylate/cross-polymer and hydroxyethylacrylate/sodium acroyldimethyl laurate copolymer.

According to some embodiments of the invention, a concentration of the emulsion stabilizer ranges from 0.1 weight percents to 3 weight percents.

According to some embodiments of the invention, the carrier further comprises a polymeric glue.

According to some embodiments of the invention, the polymeric glue is selected from the group consisting of PVP, PVP/VA and a polyquaternium.

According to some embodiments of the invention, a concentration of the polymeric glue ranges from 0.5 weight percents to 5 weight percents.

According to some embodiments of the invention, the carrier further comprises a glycolipid emulsifier.

According to some embodiments of the invention, the glycolipid emulsifier is selected from the group consisting of lauryl glucoside, caprylyl glucoside, myristyl glucoside, cetyl glucoside, stearyl glucoside and behenyl glucoside.

According to some embodiments of the invention, a concentration of the glycolipid emulsifier ranges from 0.1 weight percents to 10 weight percents.

According to some embodiments of the invention, the composition further comprises a propellant, the composition being in a form of a spray.

According to some embodiments of the invention, a concentration of the propellant ranges from 20 weight percents to 45 weight percents.

According to some embodiments of the invention, the propellant is selected from the group consisting of dimethyl ether, isobutane and a propane/butane mixture.

According to some embodiments of the invention, the hydrophobic volatile solvent is selected from the group consisting of disiloxane, dimethicone, $C_4$ cyclomethicone and $C_5$ cyclomethicone.

According to some embodiments of the invention, the disiloxane is hexamethyldisiloxane.

According to some embodiments of the invention, the dimethicone is characterized by a viscosity of about 0.65 centistokes (CSt).

According to some embodiments of the invention, the glycol is selected from the group consisting of PEG-12 dimethicone, hexylene glycol, propylene glycol, butylene glycol, ethoxydiglycol and glycerin.

According to some embodiments of the invention, the surface active agent is selected from the group consisting of Oleth-20, Ceteareth-20 and Laneth-20.

According to some embodiments of the invention, the composition is a detergent-sensitive composition.

According to some embodiments of the invention, the composition is a quick-drying composition.

As used herein the term "about" refers to ±10%.

The term "comprising" means that other steps and ingredients that do not affect the final result can be added. This term encompasses the terms "consisting of" and "consisting essentially of".

As used herein, the singular form "a", "an", and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE EMBODIMENTS

Figure 1:
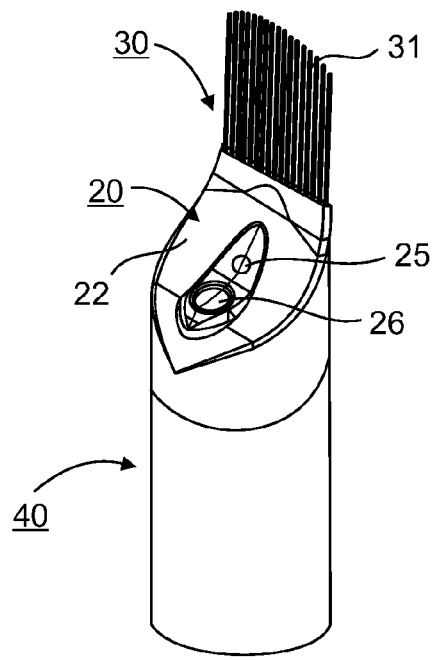
FIG. 1 is a perspective view illustrating one form of hair-dye applicator constructed in accordance with the present invention.

The present invention, in some embodiments thereof, is of a hair coloring applicator, and of hair coloring agents and compositions which can be used to color hair.

Specifically, the present invention can be used to color ("touch-up") hair along a hair line in a quick and convenient manner, particularly with a temporary hair coloring composition which is based on hair coloring agents that are substantially natural (e.g., derived from naturally-occurring substances), environmentally-friendly, and which exhibit natural hair shades, and/or a suitable volatile carrier devoid of alcohol.

The principles and operation of a hair coloring applicator according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1-5 illustrate a hair coloring applicator constructed in accordance with the present embodiments and particularly useful for touching-up hair along a hair line in a quick and convenient manner.

Figure 5:
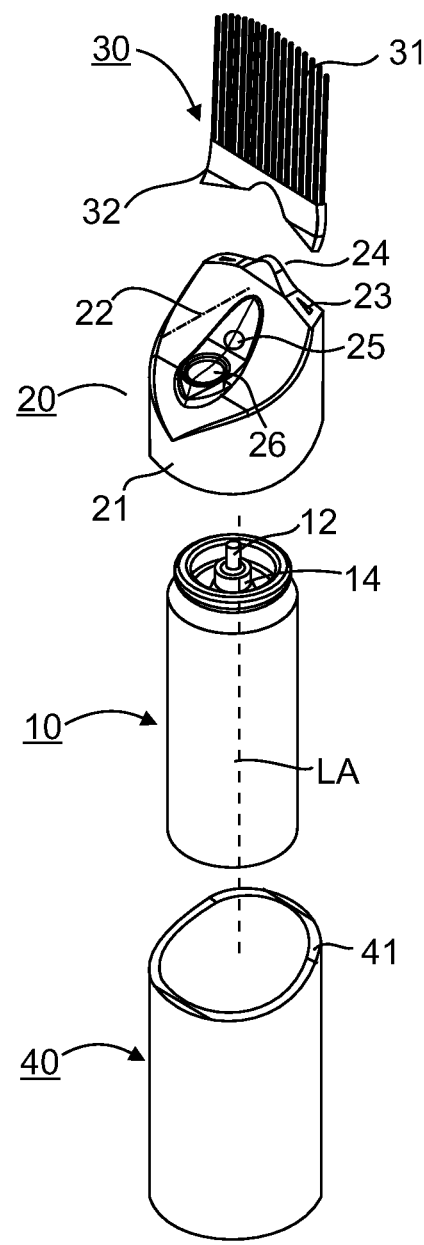
FIG. 5 is an exploded view of the main components in the hair-dye applicator of FIG. 1.
Figure 6:
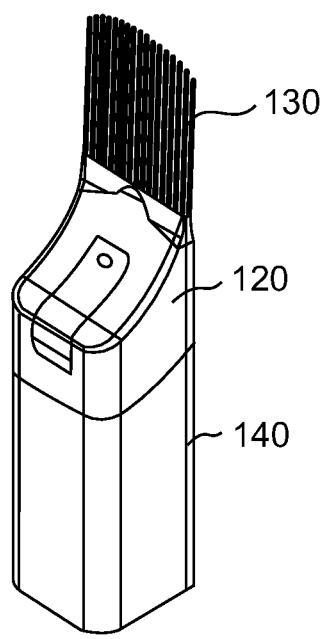
FIG. 6 is a perspective view illustrating an additional form of hair-dye applicator constructed in accordance with the present invention.
Figure 7:
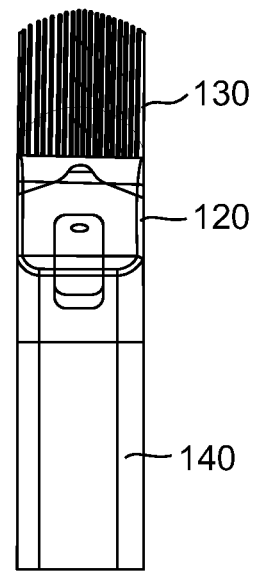
FIG. 7 is a front view of the hair-dye applicator of FIG. 6.
Figure 8:
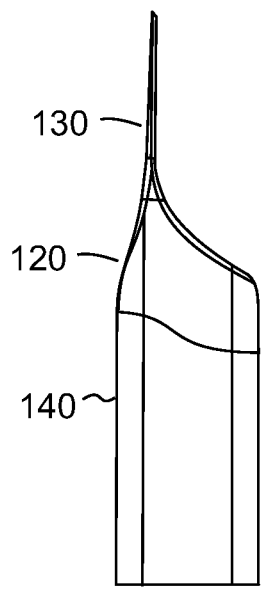
FIG. 8 is a side view of the hair-dye applicator of FIG. 6.
Figure 9:
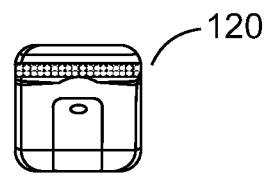
FIG. 9 is a top view of the hair-dye applicator of FIG. 6.
Figure 10:
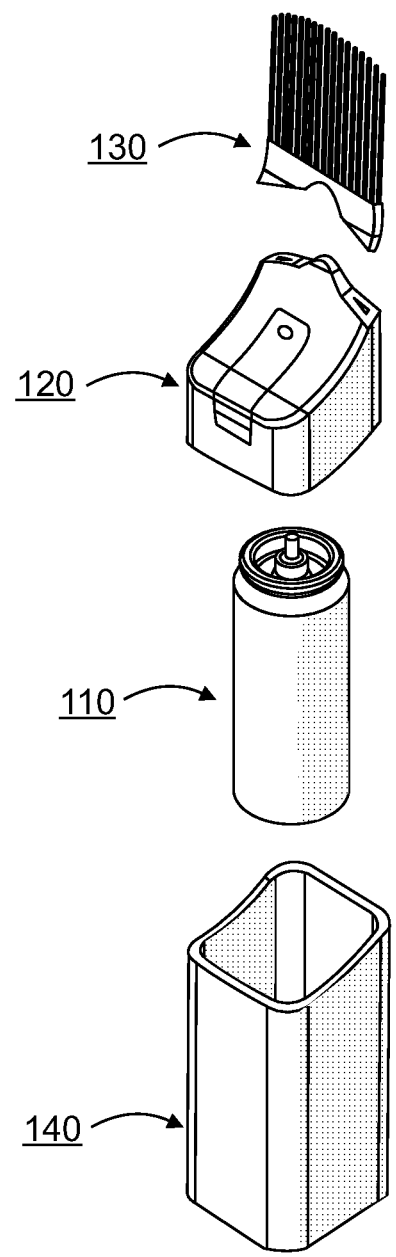
FIG. 10 is an exploded view of the main components in the hair-dye applicator of FIG. 6.

As shown particularly in the exploded view of FIG. 5, the hair coloring applicator comprises four main components: a container, generally designated 10, for containing a quantity of a hair coloring composition; an attachment 20 attachable to one end of container 10; a shield 30 carried by the attachment; and an outer housing 40 enclosing container 10 and serving as a handle for grasping and manipulating the applicator.

As clearly seen in FIG. 5, container 10 is an aerosol container of cylindrical configuration and may be of any known construction. It includes a quantity of the hair coloring composition to be dispensed, which may be in powder or liquid form; preferably, it also includes a propellant gas for dispensing the hair coloring composition in the form of a spray. One end of aerosol container 10 includes an outlet 12 in the form of a nozzle through which the composition is dispensed, and a valve indicated at 14, which is normally closed, but which is opened upon tilting or depressing nozzle 12, to dispense the composition in the form of a spray via the nozzle.

Attachment 20 is removably attachable to the end of aerosol container 10 including the nozzle 12. Attachment 20 includes a shield 30, which, as will be more particularly described below, exposes the root regions of the hairs to be touched-up, to the hair coloring composition spray dispensed via nozzle 12 when valve 14 is opened, while at the same time effectively blocking the individual's scalp from exposure to the hair coloring composition spray. Shield 30 is fixedly attached to attachment 20, but may also be removably attachable thereto for replacement or cleaning purposes. The shield and/or attachment may be constructed for one-time use, or for repeated use.

The lower end 21 of attachment 20 is of a cylindrical configuration and has an inner diameter substantially equal to the outer diameter of the aerosol container 10. One side of attachment 20 is formed with a slanted top wall 22 terminating in a top rim 23 formed with a projection 24 for receiving the shield 30 with a friction or snap fit. When attachment 20 is applied over the upper end of aerosol container 10, an opening 25 in slanted wall 22 is aligned with nozzle 12 of the aerosol container, whereas a push button 25 is aligned with valve 14 of the aerosol container. The construction is such that upon depression of the push button, nozzle 12 of the container is tilted or depressed to open valve 14, thereby to produce a spray of the hair coloring composition over the outer surface of shield 30 via opening 25 in the attachment.

As seen particularly in FIG. 5, opening 25 of attachment 20 is located between push button 26 and the shield 30 attached to peripheral wall 23 of the attachment. Nozzle 12, and opening 25 in the attachment are oriented to produce a fan-shaped spray directed towards the proximal (inner) end of the shield.

Shield 30 includes a plurality of spaced teeth 31 extending substantially parallel to the longitudinal axis LA of aerosol container 10 and integrally formed with a spline 32 extending substantially perpendicularly to the longitudinal axis LA. As shown particularly in FIG. 3, the teeth 31 of shield 30 are arrayed in a substantially linear array, which array is offset from the longitudinal axis LA of the aerosol container. Teeth 31 are of small width and thickness and are closely spaced. Preferably, they are less than 2 mm in width, thickness and spacing, and are tapered to points at their outer tips.

As will be described more particularly below, when the applicator is used for touching-up hair along a hair line, the applicator is manipulated such that surface 30a of shield 30 serves an inner surface pressed against the individual's scalp, whereas surface 30b serves as an outer surface which is exposed to the hair coloring composition spray dispensed from nozzle 12 of the aerosol container 10 via opening 22 of the attachment 20.

As shown in FIG. 5, the outer housing 40 of the applicator is also of cylindrical configuration corresponding to the cylindrical configuration of the aerosol container 10. The inner diameter of housing 40 is substantially equal to the outer diameter of aerosol container 10 so as to snugly receive the aerosol container, and thereby to act as a handle for gripping and manipulating the applicator. Preferably the upper surface 41 of outer housing 40, and the inner rim 27 of the attachment 20, are of complementary curved configurations so as to present a pleasing appearance to the applicator when all the parts are assembled as shown in FIGS. 1 and 3, for example.

Figure 2:
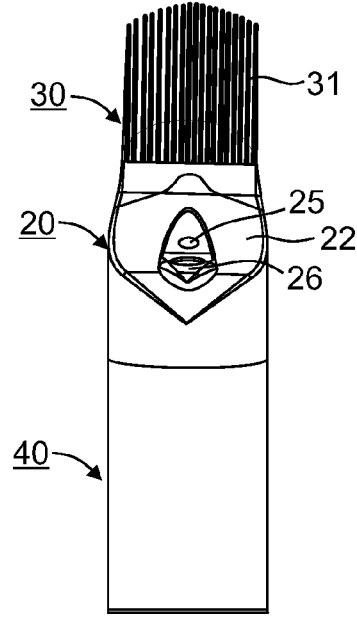
FIG. 2 is a front view of the hair-dye applicator of FIG. 1.
Figure 3:
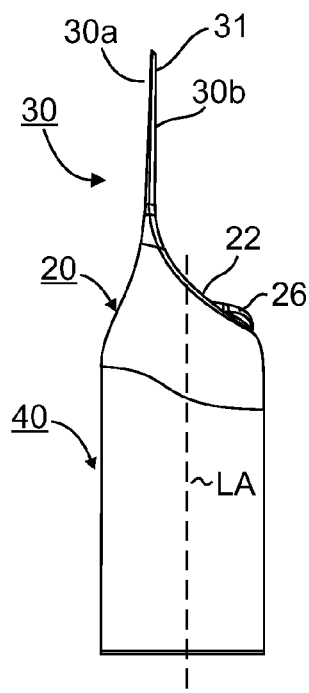
FIG. 3 is a side view of the hair-dye applicator of FIG. 1.
Figure 4:
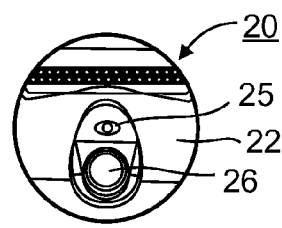
FIG. 4 is a top view of the hair-dye applicator of FIG. 1.

The manner of using the applicator of FIGS. 1-5 will be apparent from the above description. Thus, after all its parts have been assembled, as shown in FIGS. 1-3, the user grasps the outer housing 40, orients the shield 30 such that surface 30a faces and presses against the individual's scalp, and manipulates the applicator such that the root regions of the hairs along the hairline to be touched-up are received in the spaces between teeth 31. The user then depresses push button 26, to produce a spray via nozzle 12 over the outer side 30b of the shield 30, while the shield is moved along the hair line to be touched-up. The so-produced spray of hair coloring composition coats the root regions of the hairs exposed by teeth 31 at the proximal end of shield 30, whereas the remainder of the shield effectively blocks the passage of the hair coloring composition spray to the individual's scalp.

After the hair coloring composition has been depleted from aerosol container 10, the holder 40, attachment 20 and shield 30 may be disassembled and applied to a fresh aerosol container 10.

The hair coloring applicator illustrated in FIGS. 6-10 is also constructed of basically the same parts as the applicator of FIGS. 1-5, namely including an aerosol container 110 (FIG. 10), an attachment 120 applied to one end of the aerosol container, a shield 130 carried by the attachment, and an outer housing 140 enclosing aerosol container 110 and serving as a handle for gripping and manipulating the applicator.

The main difference in the applicator illustrated in FIGS. 6-10 over that illustrated in FIGS. 1-5 is that the outer housing 140, and the attachment 120, are not of a cylindrical configuration, but rather of a substantially square configuration with rounded corners, so as to present a more comfortable gripping of the applicator when manipulating it, as well as a more pleasing outer appearance to the applicator.

In all other respects, the applicator illustrated in FIGS. 6-10 is constructed and used in substantially the same manner as described above with respect to FIGS. 1-5.

While the applicator has been described with respect to two preferred embodiments, it will be appreciated that these are set forth merely for purposes of example, and that many other variations and applications of the invention may be made. For example, instead of using an aerosol container for dispensing the hair-dye in the form of a spray, a pump-type container may be used wherein the push button 26 is effective to pump out a spray of the hair-dye, rather than to open a valve permitting the propellant fluid within the container to produce the hair-dye spray. Also, the push button may be on a side wall of the container rather than on the attachment. Further, the teeth of the shield may be non-parallel to the longitudinal axis of the container, e.g., 90° or less.

The applicators described herein may contain any hair coloring composition suitable for coloring hair, preferably suitable for "touching-up" local areas of an individual's hair, and more preferably suitable for touching-up hair along a hairline of a subject.

The hair coloring composition can include any hair coloring agent(s) (pigments), formulated with a suitable carrier (e.g., designed for forming a hair coloring composition in the form of a spray). Preferably, the hair coloring composition is for temporarily coloring hair.

While the applicators described herein may contain any suitable hair coloring composition, the present inventors have developed hair-coloring agents, formulations and compositions that are particularly useful when used in the context of these and other embodiments of the present invention.

Hence, in another aspect of the present invention, there is provided a hair coloring agent which comprises a purified polymer of tannic acid having iron ions bound thereto, the purified polymer being substantially devoid of unbound iron ions. Such a hair coloring agent is also referred to herein, interchangeably as "a first hair coloring agent" and as "a purified iron-tannate polymer".

As used herein, the phrase "hair coloring agent" describes any pigment, dye or colored compound that is applied to hair in order to alter the color of the hair.

As used herein, the phrase "tannic acid" describes any compound comprising at least one catecholic group, as well as mixtures of such compounds. Thus, the compound may consist solely of a catecholic compound (e.g. catechol), or the compound may comprise a plurality of catecholic groups, with or without other chemical groups. Preferably, the tannic acid is a naturally occurring compound with low toxicity.

As used herein, the term "catecholic" describes a chemical group or compound which comprises a benzene ring substituted by at least two hydroxyls. Preferably, most of the catecholic groups or compounds comprise at least three hydroxyl substituents. Gallic acid, pyrogallol, ellagic acid, epicatechin and epigallocatechin are preferred catecholic groups, and their chemical structures are presented hereinbelow. In one embodiment, the catecholic group is gallic acid.

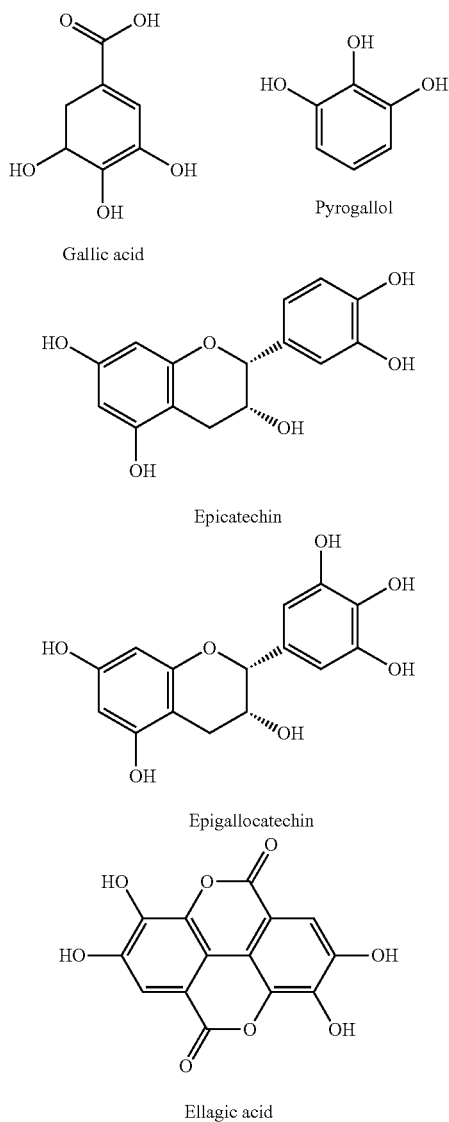

As used herein, the term "hydroxyl" is defined as an —OH group.

Preferably, the tannic acid comprises molecules having at least two catecholic groups. Typically, the catecholic groups are bound, for example, by esteric bonds, to a non-catecholic moiety, such as a sugar. The catecholic groups may also be bound directly to one another.

As used herein, the phrase "Polymer of tannic acid" encompasses any compound generated by the linking together of a plurality of molecules of tannic acid. Thus, this phrase describes a polymeric compound which comprises a plurality of tannic acid monomers (building units) that are covalently linked to one another. The size of the polymer is determined by the number of monomers composing it. The plurality of monomers can include one or more types of tannic acid monomers. The ratio between the monomers typically determines the chemical composition of the polymer. The polymer of tannic acid may comprise tannic acid monomers linked such that they are ordered in a linear structure, in a cyclic structure, and in a branched structure, as well as mixtures thereof.

As used herein, the phrase "substantially devoid of unbound iron ions" describes a compound (e.g., the tannic acid polymer) in which a concentration of unbound iron ions is below 100 ppm (weight per weight). Preferably, the concentration is below 10 ppm. The unbound iron ion concentration of an isolated, dry polymer can be characterized by dissolving the polymer in a quantity of a solvent sufficient to dissolve the polymer, followed by measurement of a concentration of unbound iron ions in the resulting solution.

As used herein, the term "bound", when describing iron ions bound to a polymer, refers to a polymer having a plurality of iron ions bound to the molecular structure of the polymer, each iron ion being bound to the polymer via at least one covalent bond, coordinative (organometallic) bond and/or electrostatic interaction.

Without being bound to any particular theory, it is believed that at least some of the iron ions are bound via an organometallic bond.

As used herein, the phrase "unbound iron ion" describes an iron ion that is not bound to tannic acid or a polymer of tannic acid, as defined hereinabove. Thus, an iron ion that is bound to ions such as chloride, sulfate, citrate and hydroxide, which do not form a part of the polymer, would be considered herein as unbound. Preferably, an unbound iron ion is readily capable of reacting with surrounding molecules, and hence may readily be detected by an assay for that iron ion. One skilled in the art will be familiar with various assays for determining the presence of an unbound iron ion. For example, iron(III) ion may be assayed via reaction with ferrocyanide.

According to an optional embodiment of the present invention, both the iron ions bound to the polymer of tannic acid and the unbound iron ions absent from the hair coloring agent are iron(III) ions (also known as ferric ions), e.g. $Fe^{3+}$. Iron (III) ions are oxidative and corrosive, and can irritate the underlying skin and damage hair. Preferably, iron(II) ions (also known as ferrous ions) are also absent from the hair coloring agent. Iron(II) is an effective generator of free radicals, and can induce damage and/or bleaching of hair. Iron ions can also alter the pigmentation of skin. The undesirable side effects of iron ions are inhibited when the iron is bound, so only unbound iron ions are of concern in the context of a hair coloring agent.

According to an embodiment of the present invention, the iron ions bound to the polymer of tannic acid substantially consist of iron(III) ions. A small amount of the bound iron ions may be other than iron(III).

As is well known in the art, polymerization may result in a variety of polymer compounds, which may have different colors, as well as different molecular weights.

According to an embodiment of the present invention, the abovementioned first hair coloring agent is characterized by a black-violet color.

According to a further embodiment of the present invention, the abovementioned purified iron-tannate polymer has an average molecular weight of at least 10 kilodaltons (kDa). Such an average molecular weight may be determined for example, by observing whether the most of the polymer is retained by a filter (e.g., a membrane) which selectively allows the passage of molecules smaller than 10 kDa, as demonstrated hereinbelow in the Examples.

The hair coloring agents according to embodiments of the present invention are contemplated for use in temporary hair coloring compositions. For this use, it is preferable that the hair coloring agents be water-soluble, in order to facilitate their application and removal.

As used herein, the term "water-soluble" describes a substance which is capable of forming a homogeneous mixture in water. The homogeneous mixture may be a solution, in which the substance dissolves in water, or it may be a colloidal dispersion, in which small particles of the substance are uniformly dispersed throughout the water. The average diameter of particles in a colloidal dispersion is preferably less than 1 micron. One of skill in the art will appreciate the similarity between a large molecule dissolved in solution and a colloidal particle.

As used herein, the phrase "temporary hair coloring composition" describes a hair coloring composition wherein the hair coloring agent(s) therein does not substantially penetrate the hair shafts, but rather attaches to the outer surface thereof, and is not meant to be oxidized following application onto the hair. Such hair coloring agents typically may be removed more easily than hair coloring agents which effectively penetrate the hair shafts and/or are fixated in the hair by oxidization, and hence, are considered "temporary". Hence, according to an embodiment of the present invention, the purified iron-tannate polymer hair coloring agent is water-soluble.

It is noted herein that currently known iron-tannates typically have limited water-solubility. A water-soluble iron-tannate may be obtained by various means. For example, a water-soluble iron-tannate polymer may be obtained by exposing an iron-tannate to water and isolating the iron-tannate which dissolves in the water, thereby separating the water-soluble iron-tannate from the water-insoluble iron-tannate. Preferably, the hair coloring agent has a water-solubility of at least 5 weight percents, more preferably, at least 10 weight percents, still more preferably, at least 20 weight percents, and most preferably, at least 25 weight percents.

As used herein, the term "water-solubility" describes the maximal concentration of a substance in water, at which the substance is water-soluble, as defined hereinabove.

The inventors have developed a novel process for preparing the abovementioned purified iron-tannate polymers, devoid of unbound iron ions.

Hence, according to another aspect of the present invention, there is provided a process for preparing the first hair-coloring agent described herein, the process being effected by reacting a tannic acid and an iron salt, to thereby obtain a polymer of tannic acid having iron ions bound thereto and purifying the polymer to obtain the hair coloring agent. Preferably, the iron salt is a ferric (i.e. iron(III)) iron salt. An exemplary ferric salt is ferric ammonium citrate.

According to an embodiment of the present invention, the tannic acid and iron salt are reacted in an aqueous solution.

According to another embodiment, the concentration of the tannic acid in the aqueous solution ranges from 10 weight percents to 75 weight percents, preferably from 20 weight percents to 50 weight percents, more preferably from 25 weight percents to 30 weight percents.

In one embodiment, a weight ratio of iron ions in the iron salt and the tannic acid ranges from 1 part iron ions to 5 parts tannic acid to 1 part iron ions to 500 parts tannic acid, preferably from 1 part iron ions to 15 parts tannic acid to 1 part iron ions to 150 parts tannic acid, more preferably from 1 part iron ions to 30 parts tannic acid to 1 part iron ions to 80 parts tannic acid, more preferably from 1 part iron ions to 45 parts tannic acid to 1 part iron ions to 70 parts tannic acid, optionally from 1 part iron ions to 55 parts tannic acid to 1 part iron ions to 60 parts tannic acid.

Purifying the iron tannate polymer can be effected by various routes. Exemplary purification procedures include, but are not limited to, gel-exclusion chromatography, ion-exchange chromatography, dialysis, ultrafiltration, and precipitation of either the iron-tannate polymer or the unbound iron ions. According to an embodiment of the present invention, the purifying of the iron-tannate polymer comprises purification by gel exclusion chromatography and/or by ultrafiltration.

In an exemplary purification procedure, the first hair coloring agent is eluted by an aqueous solution. Elution by aqueous solution additionally serves to isolate a water-soluble fraction of the polymer. The first hair coloring agent is obtained by collecting at least one substantially colored fraction eluted by the aqueous solution. As the desired compound is colored, it is particularly simple and convenient to identify the fraction(s) comprising the desired compound by color. However, any suitable method for identifying the appropriate fraction(s) may be used.

Alternatively, any other method capable of separating the polymer from unbound iron ions may be used. Preferably, the method also selects for a water-soluble fraction.

The first hair coloring agent may be concentrated and/or isolated by evaporating some or all of the water from the fraction(s) comprising the hair coloring agent.

The purified iron-tannate polymer hair coloring agent described herein imparts a dark, typically black-violet color to hair.

The purified iron-tannate polymer hair coloring agent described herein may be produced using safe, natural, environmentally friendly compounds (e.g. by using a naturally occurring tannic acid). Its incorporation in a hair coloring composition therefore results in a safe, natural, environmental-friendly composition.

According to a further aspect of the present invention, there is provided a use of the abovementioned first hair coloring agent in the manufacture of a hair coloring composition, as is detailed hereinbelow.

As discussed hereinabove, melanoidins are a family of brownish, colored compounds that result from the interaction between sugars and amino acids under moderate heat. Melanoidins are responsible for much of the browning and flavor of cooked foods, and hence are recognized as completely safe, natural, and environmentally friendly agents. However, melanoidins have not been disclosed as hair colorants heretofore.

The present inventors have envisioned that melanoidins can be utilized as hair coloring agents, and particularly as hair coloring agents for temporary hair coloring.

Hence, according to another aspect of the embodiments of the present invention, there is provided a use of a composition-of-matter which comprises a condensation polymer of at least one reducing carbohydrate and at least one amino acid as a hair coloring agent. Such a composition-of-matter is also referred to herein interchangeably as "a second hair coloring agent", a "melanoidin", or as a "melanoidin condensation polymer".

According to an embodiment of the present invention, there is provided a use of the melanoidin condensation polymer described herein in the manufacture of a hair coloring composition.

As used herein, the phrase "condensation polymer" describes a polymer, as defined herein, formed by interaction between monomer molecules, wherein the reaction linking the monomer molecules together to form a polymer further results in the formation of a (released) water molecule. For example, an amine group in an amino acid may react with a carbonyl group (e.g., aldehyde) in a reducing sugar to form a water molecule and a molecule (which may react further) comprising an amino acid moiety linked to a carbohydrate moiety via an imine bond.

As used herein, the term "carbohydrate" is defined as a compound consisting essentially of one or more monosaccharide moieties, as defined hereinbelow. Thus for example, the carbohydrate may be a monosaccharide, a polymer of monosaccharides (i.e. a polysaccharide), an oligomer of monosaccharides (i.e. an oligosaccharide), a trimer or a dimer of monosaccharides. The monosaccharide units in a carbohydrate may be the same or different.

The term "monosaccharide", as used herein and as is well known in the art, refers to a simple form of a sugar that consists of a single monosaccharide unit which cannot be further decomposed to smaller monosaccharide building blocks or moieties. Most common examples of monosaccharides include glucose (dextrose), fructose, galactose, mannose, and ribose.

Monosaccharides can be classified according to the number of carbon atoms of the carbohydrate, i.e., triose, having 3 carbon atoms such as glyceraldehyde and dihydroxyacetone; tetrose, having 4 carbon atoms such as erythrose, threose and erythrulose; pentose, having 5 carbon atoms such as arabinose, lyxose, ribose, xylose, ribulose and xylulose; hexose, having 6 carbon atoms such as allose, altrose, galactose, glucose, gulose, idose, mannose, talose, fructose, psicose, sorbose and tagatose; heptose, having 7 carbon atoms such as mannoheptulose, sedoheptulose; octose, having 8 carbon atoms such as 2-keto-3-deoxy-manno-octonate; nonose, having 9 carbon atoms such as sialose; and decose, having 10 carbon atoms.

Alternatively, the monosaccharide can be a monosaccharide derivative, in which the monosaccharide unit comprises one or more substituents other than hydroxyls. Such derivatives can be, but are not limited to, ethers, esters, acids, phosphates and amino monosaccharides.

As used herein, the term "reducing", when used to describe a carbohydrate, refers to a carbohydrate comprising at least one carbonyl, namely aldehyde and/or ketone, group. The aldehyde and ketone may be in a form which is in equilibrium with an aldehyde or ketone in aqueous solution (e.g. a hemiacetal or geminal diol, respectively). Reducing carbohydrates are so named because they can typically undergo oxidation by reagents such as metal ions. However, reducing carbohydrates are defined herein according to structure, as defined hereinabove, and not by experimentally determining the reductive capability thereof.

According to an embodiment of the present invention, the reducing carbohydrate is a sugar. Optionally the sugar is a monosaccharide. Hexoses are exemplary monosaccharides.

An exemplary hexose is glucose. Glucose is a cheap, widely available, safe, environmentally friendly and naturally occurring carbohydrate.

As used herein, the term "sugar" refers to a compound comprising 1, 2 or 3 monosaccharide moieties linked to each other.

As used herein, the phrase "amino acid" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the phrase "amino acid" includes both D- and L-amino acids.

Exemplary amino acids therefore include, but are not limited to, alanine, arginine, asparagine, aspartic acid, cysteine, glutamate, glutamine, glycine, histidine, isoleucine, leucine, lysine, methionine, phenylalanine, proline, serine, threonine, tryptophan, tyrosine, valine, selenocysteine, pyrrolysine, citrulline, and hydroxyproline, as well as mixtures thereof (e.g. hydrolyzed protein).

According to an embodiment of the present invention, the amino acid is glycine.

Thus, in an exemplary embodiment of the present invention, the melanoidin is a condensation polymer formed from glucose and glycine.

According to an embodiment of the present invention, a weight ratio of the reducing carbohydrate and the amino acid in the condensation polymer ranges from 3:1 to 1:3. Preferably, the weight ratio ranges from 2:1 to 1:2, more preferably, from 1.5:1 to 1:1.5, and more preferably the weight ratio is about 1:1. The weight ratio refers to the relative weights of the reducing carbohydrate and the amino acid before they are reacted to produce the condensation polymer.

The melanoidin described herein can therefore be a condensation polymer formed from any amino acid, as described herein and any reducing carbohydrate, as described herein.

In an exemplary embodiment, the condensation polymer is prepared by heating a mixture of an amino acid, as described herein and a reducing carbohydrate, as described herein.

In an exemplary embodiment, the heating is performed at a temperature ranging from 100° C. to 150° C., preferably from 110° C. to 140° C., and more preferably from 120° C. to 130° C.

According an embodiment of the present invention, the melanoidin condensation polymer is a water-soluble polymer.

The purified iron-tannate polymer and melanoidin hair coloring agents presented herein may be used to color hair by inclusion of the hair coloring agent in a hair coloring composition designed to be applied to the hair.

In order to manufacture hair coloring compositions which may provide a variety of natural shades to hair, it is desirable to have a reddish hair coloring agent, as a wide variety of natural hair shades may be obtained by mixing a reddish color and a blackish color in various proportions. This technique mimics natural hair colors, which result from mixtures of black, brown and red melanins in various proportions.

Hence, in another aspect of the embodiments of the present invention, there is provided a hair coloring composition which comprises any of the hair coloring agents presented herein (e.g. the purified iron-tannate polymer and the melanoidin composition-of-matter) and a suitable carrier.

As used herein, the phrase "suitable carrier" refers to a carrier or a diluent (e.g., a solution or powder) to which a hair coloring agent may be added, and which can facilitate the application of a hair coloring agent onto a subject's hair. A suitable carrier typically has no detrimental effect when applied to the hair or skin of a human, and has no unpleasant appearance, feel and/or aroma. Suitable carriers also do not cause significant irritation to a subject and do not abrogate the activity (e.g., hair coloring function) and properties of the hair coloring agent.

In an embodiment of the present invention, the hair coloring composition described herein is designed for coloring white or gray hair. Thus, the hair coloring composition is capable of providing a natural hair color when applied to white or gray hair.

In a further embodiment of the present invention, the hair coloring composition is a temporary hair coloring composition.

In an embodiment of the present invention, the hair coloring composition is detergent-sensitive.

As used herein, the phrase "detergent-sensitive" describes a hair coloring composition that is removed by washing with a detergent. That is, the color of the hair following washing with a detergent is substantially identical to the hair color prior to application of the hair coloring composition. Preferably, the composition is water-resistant, that is, it withstands washing without a detergent, e.g. with water alone. That is, white or gray hair that is colored with the hair coloring composition remains substantially non-white and non-gray following washing with water without a detergent. Such a property advantageously provides the ability to remove the composition completely when desired, e.g. by shampooing, but is not removed by mere exposure to water, such as in the form of rain.

The composition may also be sensitive to a detergent which is not present in many shampoos, while being insensitive to other detergents, such that the composition may be removed completely from hair when desired by using a detergent to which the composition is sensitive (e.g., in the form of a shampoo), while shampoos to which the composition is not sensitive may be used to clean the hair when removal of the composition from the hair is not desired.

As used herein, the term "detergent" is defined as any compound commonly used in combination with water to clean, particularly to clean an individual's head, such as compounds used as shampoo and/or soap ingredients.

In an embodiment of the present invention, the hair coloring composition is useful for touching-up hair along a hairline of an individual. For example, the hair coloring composition should be capable of being simply and easily applied to the hairline by a normal person with no relevant expertise, and should have no undesired effects on the skin near the hairline (e.g. staining, irritation). In particular, the hair coloring composition should be capable of being simply and easily applied to white and/or gray hair along a hairline, such that no white and/or gray hair remains visible along the hairline following application.

Depending on the desired color which a hair coloring composition imparts when applied to an individual's hair, the hair coloring composition described herein can comprise either or both the purified iron-tannate hair polymer hair coloring agent and a melanoidin hair coloring agent described herein. When both hair coloring agents are utilized, the weight ratio therebetween typically determines the final color imparted by the hair coloring composition, as exemplified in the Examples hereinbelow. The color may also be determined by using different precursors (i.e. different reducing carbohydrates and/or different amino acids) for producing melanoidin, resulting in melanoidins with different shades, which in turn may be mixed with an iron-tannate polymer so as to obtain different hair color compositions. One skilled in the art will be capable of selecting a melanoidin with the desired shade through routine experimentation.

As will be apparent to one skilled in the art, the final color of the colored hair will depend on the initial hair color. Various techniques may be used to select an appropriate hair coloring composition for obtaining a desired hair color. For example, U.S. Pat. No. 7,110,117 describes a method of determining the expected color of a given hair sample following a hypothetical hair-coloring treatment. The hair coloring compositions described herein can be formulated in any form that is suitable for application to hair.

By selecting the appropriate carrier and optionally other ingredients that can be included in the composition, as is detailed hereinbelow, the hair coloring compositions described herein may be formulated into any form typically employed for topical application such as application to hair. Hence, the hair coloring compositions can be, for example, in a form of a cream, an ointment, a paste, a gel, a lotion, a milk, a suspension, an aerosol, a spray, a foam, a shampoo, a hair conditioner, a swab, a pledget, a pad, and a soap.

Ointments are semisolid preparations, typically based on vegetable oil (e.g. shea butter and/or cocoa butter), petrolatum or petroleum derivatives. The specific ointment base to be used is one that provides for optimum delivery for the hair coloring agent chosen for a given formulation, and, preferably, provides for other desired characteristics as well (e.g., emolliency). As with other carriers or vehicles, an ointment base should be inert, stable, nonirritating and nonsensitizing.

Lotions are preparations that may to be applied to the hair without friction. Lotions are typically liquid or semiliquid preparations in which solid particles, including the hair coloring agent, are present in a water or alcohol base. Lotions are typically preferred for treating large areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the hair coloring agent in contact with the hair.

Creams are viscous liquids or semisolid emulsions, either oil-in-water or water-in-oil. Cream bases typically contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant.

Pastes are semisolid dosage forms in which the hair coloring agent is suspended in a suitable base. Depending on the nature of the base, pastes are divided between fatty pastes or those made from a single-phase aqueous gels. The base in a fatty paste is generally petrolatum, hydrophilic petrolatum and the like. The pastes made from single-phase aqueous gels generally incorporate carboxymethylcellulose or the like as a base.

Gel formulations are semisolid, suspension-type systems. Single-phase gels contain organic macromolecules distributed substantially uniformly throughout the carrier liquid, which is typically aqueous, but also, preferably, contains a non-aqueous solvent and, optionally, an oil. Preferred organic macromolecules, i.e., gelling agents, are crosslinked acrylic acid polymers such as the family of carbomer polymers, e.g., carboxypolyalkylenes that may be obtained commercially under the trademark CARBOPOL™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the hair coloring agent in an aqueous and/or volatile solvent solution which can be misted onto the hair for delivery. Such sprays include those formulated to provide for concentration of the hair coloring agent solution at the site of administration following delivery, e.g., the spray solution can be primarily composed of a volatile liquid in which the hair coloring agent can be dissolved. Upon delivery to the hair, the carrier evaporates, leaving concentrated hair coloring agent at the site of administration.

Foam compositions are typically formulated in a single or multiple phase liquid form and housed in a suitable container, optionally together with a propellant which facilitates the expulsion of the composition from the container, thus transforming it into foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high volatile solvent content which, upon application to the hair of a user, quickly evaporates, leaving concentrated hair coloring agent on the hair.

Representative examples of suitable carriers according to embodiments of the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic compositions.

The chemical composition of the carrier is typically selected according to the desired form of the hair coloring composition. Further, the chemical composition of the carrier is selected so as to suit the desired purpose of the hair coloring composition.

Preferred carriers for use in a temporary hair coloring composition are therefore selected such that they are quick-drying, facilitate the spreading of the composition through the hair but minimize dripping out of the hair and/or onto the scalp, are non-harmful, and do not cause the hair to have an unappealing feel, appearance or aroma.

For example, dripping may be prevented by using a viscous carrier (e.g. cream, gel, foam), which is fluid enough to facilitate spreading through the hair, but sufficiently viscous so as to avoid dripping, as well as by using a quick-drying spray carrier, in which the carrier is sprayed onto the desired location, and then dries up before dripping out of the desired location.

Reflective compounds, such as silicone oils, may be included in a carrier to provide hair with a glossy appearance.

Carriers suitable for temporary hair coloring compositions may also comprise a compound that binds the hair coloring agent to the hair so that the coloring agent does not come off by rubbing. Typically, such a compound is a polymer which binds hair. For example, U.S. Pat. Nos. 6,506,374 and 5,821,240 teach carriers which prevent rubbing off of the hair coloring agent.

According to an embodiment of this aspect of the present invention, the hair coloring composition presented herein is in the form of a spray.

The present inventors have developed a carrier particularly suitable for use in temporary hair coloring compositions, such as those comprising the abovementioned hair coloring agents, as well as any composition applied with an applicator described herein.

Hence, in another aspect of the embodiments of the present invention, there is provided a hair coloring composition comprising at least one hair coloring agent and a carrier, wherein the carrier comprises:

(i) a hydrophobic volatile solvent, preferably in a concentration that ranges from 20 to 60 weight percents of the carrier, more preferably from 30 to 50 weight percents, and more preferably from 35 to 40 weight percents;

(ii) water, preferably in a concentration that ranges from 20 to 60 weight percents of the carrier;

(iii) a glycol, preferably in a concentration that ranges from 0.5 to 10 weight percents of the carrier, more preferably from 2 to 6 weight percents, and more preferably about 5 weight percents; and (iv) a surface active agent, preferably in a concentration that ranges from 0.1 to 7.5 weight percents of the carrier, more preferably from 0.5 to 5 weight percents, still more preferably from 2 to 4 weight percents, and more preferably from 2.5 to 3 weight percents;

wherein the carrier is substantially devoid of an alcohol.

As used herein, the term "hydrophobic" describes a compound that is substantially immiscible with water.

As used herein, the term "hydrophilic" describes a compound that is miscible with water.

As used herein, the term "volatile" describes a compound which at ambient conditions (e.g., room temperature, atmospheric pressure) evaporates more rapidly than does water. Preferably, the compound, after being applied to hair, is substantially evaporated within less than 1 hour, more preferably within less than 10 minutes, more preferably, within less than 2 minutes, still more preferably, within less than 30 seconds, and most preferably, within 10 seconds. Exemplary hydrophobic volatile solvents include disiloxane, dimethicone, $C_4$ cyclomethicone and $C_5$ cyclomethicone.

As used herein, the term "disiloxane" describes a compound having the formula $R_3Si-O-SiR_3$, wherein the R groups may be the same or different, and are independently selected from the group consisting of hydrogen and C1-5 alkyl. Hexamethyldisiloxane is an exemplary disiloxane suitable for use in the context of the embodiments of this aspect of the present invention.

As used herein, the term "dimethicone" describes a compound having the formula $CH_3[-Si(CH_3)_2-O]_n-Si(CH_3)_3$, wherein n may be any positive integer, provided that the dimethicone is volatile, as defined hereinabove. Preferably, the dimethicone is characterized by a viscosity of about 0.65 centistokes (CSt).

As used herein, the term "cyclomethicone" describes a compound having a cyclic structure of the formula $[-Si(CH_3)_2-O-]_n$, wherein n may any positive integer above 1, provided that the cyclomethicone is volatile, as defined hereinabove. As used herein, the phrase "$C_4$ cyclomethicone" describes a cyclomethicone wherein n is 4, whereas the phrase "$C_5$ cyclomethicone" describes a cyclomethicone in which n is 5.

As used herein, the term "glycol" encompasses simple glycols, composed of any organic compound having two adjacent non-aromatic carbon atoms, each being substituted by a hydroxyl group, as well as compounds comprising two or more glycol moieties linked to one another by one or more ether bond, such as in the case of dialkylene glycols (e.g. diethylene glycol) and polyalkylene glycols (e.g., polyethylene glycol), as well as etherified derivatives thereof.

As used herein, the term "ether" refers to an alkyl-O-alkyl group.

The term "alkyl" as used herein, describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms.

As used herein, the phrase "etherified derivative" describes a derivative of a compound in which a hydroxyl is replaced by an alkoxy group, as defined herein.

As used herein, the term "alkoxy" refers to a —O-alkyl group.

Exemplary glycols that are suitable for use in the context of these embodiments of the present invention include, without limitation, polyethylene glycol-12 dimethicone (PEG-12 dimethicone), hexylene glycol, propylene glycol, butylene glycol, ethoxydiglycol (diethylene glycol monoethyl ether) and glycerin.

The phrase "surface active agent" is used herein according to the art-recognized definition. A surface active agent is an agent capable of reducing the surface tension of a liquid. Typically, surface active agents comprise a hydrophobic moiety and a hydrophilic moiety. Exemplary surface active agents that are suitable for use in the context of these embodiments of the present invention include, without limitation, Oleth-20, Ceteareth-20 and Laneth-20.

As discussed hereinabove, the hair coloring composition described herein is advantageous for being substantially devoid of an alcohol.

As used herein, the term "alcohol" describes an organic compound having one hydroxyl group, and no more than one ether group.

The phrase "substantially devoid of alcohol", as used in the context of these embodiments, describes a concentration of alcohol which is no more than 1 weight percent, preferably no more than 0.5 weight percents, and more preferably, no more than 0.1 weight percents of the total weight of the composition. More preferably, the alcohol concentration is zero.

A volatile solvent is particularly advantageous in a hair coloring composition, as the solvent initially facilitates the application and spreading of the hair coloring agent through the hair, yet evaporates quickly, leaving a dry agent in place, and thus preventing undesired smears and stains, as well as an undesired wet appearance of the hair.

Alcohols are commonly used as volatile solvents for hair coloring compositions, particularly ethyl, propyl and butyl alcohols. Thus, the lack of an alcohol, and the presence of a non-alcoholic volatile solvent represent a significant advantage of the embodiments of the present invention, in that the advantages of volatility are retained without having the disadvantages of alcohols.

According to an optional embodiment of the present invention, the carrier further comprises an emulsion stabilizer. Preferably, a concentration of emulsion stabilizer in the carrier ranges from 0.1 weight percents to 3 weight percents.

As used herein, the phrase "emulsion stabilizer" describes any compound which substantially reduces the rate of agglomeration, coalescence and/or sinking or rising of droplets of a dispersed phase of an emulsion. An emulsion stabilizer may be a surface active agent or a solid particle, both of which increase the stability of emulsions. An emulsion stabilizer may also be an agent, such as a thickener or a gelling agent, which increases the viscosity of an emulsion, thereby stabilizing the emulsion by limiting the movement of the particles therein. Preferably, the emulsion stabilizer is a polymer. More preferably, the emulsion stabilizer is a polymer selected from the group consisting of acrylate/C10-30-alkyl acrylate/cross-polymer and hydroxyethylacrylate/sodium acroyldimethyl laurate copolymer. These polymers are sold commercially, for example, under the trade names PEMULEN® and CARBOPOL®, and SIMULGEL™, respectively.

In an embodiment of the present invention, the carrier further comprises a polymeric glue.

As used herein, the phrase "polymeric glue" describes a polymer or a cationic compound identified as promoting adhesion of a composition to a hair.

Exemplary polymeric glues include, but are not limited to, polyvinyl pyrrolidone (PVP), a copolymer of polyvinyl pyrrolidone and polyvinyl alcohol, and a polyquaternium. Non-polymeric cationic compounds, such as a quaternium, may also be used. A polyquaternium and a quaternium may be any of several compounds so designated according to the International Nomenclature for Cosmetic Ingredients. Exemplary polyquaterniums include polyquaternium 1, polyquaternium 6, polyquaternium 7, polyquaternium 10, polyquaternium 11, polyquaternium 22 and polyquaternium 39. An exemplary quaternium is quaternium 80. Preferably, a concentration of polymeric glue ranges from 0.5 weight percents to 5 weight percents of the carrier, more preferably from 0.5 to 1.5 weight percents.

In an optional embodiment of the present invention, the carrier further comprises a glycolipid emulsifier.

As used herein, the phrase "glycolipid emulsifier" encompasses any compound comprising a carbohydrate moiety and at least one fatty acid moiety, identified as being an emulsion stabilizer, as defined hereinabove. Exemplary glycolipid emulsifiers include lauryl glucoside, caprylyl glucoside, myristyl glucoside, cetyl glucoside, stearyl glucoside and behenyl glucoside. Preferably, a concentration of glycolipid emulsifier ranges from 0.1 weight percents to 10 weight percents of the carrier, more preferably from 1 to 6 weight percents.

It is to be understood that in the case of a compound which fits the definition of more than one of the abovementioned components of a composition, for example, a glycolipid emulsifier that is also a surface active agent and an emulsion stabilizer, the weight of the compound is not to be counted as contributing to the weight concentration of more than one component. However, a fraction of the concentration of a compound may be counted as one component, with another fraction of the concentration being counted as another component.

In addition, the abovementioned components of a composition may consist of the sum of any two or more compounds that fit the definition of that component.

In an embodiment of the present invention, the hair coloring composition is in the form of a spray and further comprises a propellant, as defined hereinabove. Preferably, a concentration of propellant ranges from 20 weight percents to 45 weight percents of the composition, more preferably from 25 to 40 weight percents, and more preferably from 30 to 35 weight percents. A propellant may be any compound with a boiling temperature moderately lower than room temperature at atmospheric pressure, which is thus in a vapor/liquid equilibrium when stored at pressures above atmospheric pressure. The abovementioned weight concentration of propellant includes both the vapor and liquid phases of the propellant. Exemplary propellants include, without limitation, dimethyl ether, isobutane and a propane/butane mixture.

The carrier described herein can be used with any hair coloring agent known in the art.

In one embodiment of the present invention, the hair coloring composition comprises a carrier as described herein and one or more of the first and second hair coloring agents as described herein.

According to some embodiments of the present invention, each of the hair coloring compositions described herein is identified for use in temporary hair coloring and/or in coloring white or gray hair.

According to some embodiments of the present invention, each of the hair coloring compositions described herein is identified for use in touching-up hair along a hairline of an individual.

In one embodiment of the present invention, any of the hair coloring compositions described herein is packaged in an applicator adapted for dispensing the composition onto hair, and identified for use in hair coloring, as described hereinabove.

Any applicator suitable for applying a composition onto hair may be used. Exemplary applicators include, but are not limited to, a wick-type applicator, a squeeze bottle, an aerosol container, a comb-type applicator, a drop dispenser and a pump-type applicator.

As used herein, the phrase "wick-type applicator" encompasses any applicator comprising a wick which absorbs a quantity of a liquid composition, wherein the composition may be applied to a surface by contacting the wick with the absorbed composition to the surface. The quantity of the composition absorbed in the wick may be replenished, for example, by dipping the wick into a quantity of the composition stored in a container, or by part of the wick being in continuous contact with the composition in a container, the composition being drawn into the wick via absorption by the wick. The container containing the composition may serve as a component of the applicator along with the wick.

As used herein, the term "wick" describes an article-of-manufacturing capable of absorbing a liquid and of allowing the liquid to escape from the surface of the article-of-manufacturing.

As used herein, the phrase "squeeze bottle" encompasses any applicator comprising a container for storing a composition, the container having at least one flexible wall, wherein the composition may be forced out of the container by applying force (e.g. squeezing) to the flexible wall(s) of the container. Typically, the container includes a valve that allows a composition to exit the container under a certain pressure (such as the pressure generated by applying force to the flexible wall of the container), but which prevents composition from leaving the container in the absence of such pressure.

As used herein, the phrase "comb-type applicator" encompasses any applicator comprising a comb or a brush, the comb or brush having a quantity of composition adhered thereto, wherein the composition may be applied to a surface by contacting the comb or brush to the surface. The quantity of composition which is adhered to the comb or brush may be replenished by contacting the comb or brush with a composition stored in a container. The container may serve as a component of the applicator.

As used herein, the phrase "drop dispenser" encompasses any applicator comprising a container containing therein a liquid composition, the container having a small opening which allows the passage of a small quantity of the composition from the inside of the container through the opening to the outer surface of the container, thereby resulting in a small quantity of composition (i.e. a drop) on the outer surface of the container. The drop of composition may be applied to a surface by contacting the drop with the surface. The liquid composition in the container may be replenished from a larger quantity of composition stored in a larger container, which may serve as a component of the applicator.

As defined herein, the phrase "pump-type applicator" encompasses any applicator comprising a container for storing a composition with a pump attached thereto, wherein the composition may be forced out of the container by a pressure applied by the pump. The container may include a valve that allows a composition to exit the container under a pressure applied by the pump, but which prevents composition from leaving the container in the absence of such pressure. The pressure applied by the pump may be generated by any means, including, but not limited to, by hand (e.g. a syringe), by a spring, by an electronic motor, or by a pressurized fluid.

As used herein, the phrase "aerosol container", when used to describe an applicator, encompasses any applicator comprising an aerosol container, as this phrase has been defined hereinabove. An applicator described as an aerosol container may include additional components besides the aerosol container.

When the hair coloring composition is a composition useful for coloring white and/or gray hair, the composition is preferably identified as such.

When the hair coloring composition is a composition useful for temporary hair coloring, the composition is preferably identified as such.

When the hair coloring composition is a composition useful for touching-up hair along a hairline of an individual, the composition is preferably identified as such.

The applicators, hair coloring agents and hair coloring compositions described hereinabove are particularly advantageous when used in combination.

Hence, according to another aspect of the present invention, there is provided an applicator as described hereinabove, wherein a hair coloring composition to be contained therein comprises a suitable carrier and at least one hair coloring agent selected from the group consisting of a first hair coloring agent which comprises a purified polymer of tannic acid having iron ions bound thereto, being substantially devoid of unbound iron ions, and a second hair coloring agent which comprises a condensation polymer of a reducing carbohydrate and an amino acid, as these hair coloring agents are described herein.

The features of the composition are as described hereinabove. Preferably, in embodiments comprising an applicator which releases a composition in the form of a spray, the composition to be contained therein is in the form of a spray, as described hereinabove.

In another aspect of the present invention, there is provided an applicator, as described hereinabove, wherein the hair coloring composition to be contained therein comprises at least one hair coloring agent and a carrier which comprises a hydrophobic volatile solvent, water, a glycol and a surface active agent, as described hereinabove.

The features of the composition are as described hereinabove. Preferably, in embodiments comprising an applicator which releases a composition in the form of a spray, the composition to be contained therein is in the form of a spray, as described hereinabove.

In another aspect of the present invention, there is provided a hair coloring composition comprising both a carrier described hereinabove and at least one hair coloring agent described hereinabove.

The optional and preferable features of the composition are as described hereinabove.

In a preferred embodiment of the present invention, an applicator described hereinabove is combined with a hair coloring composition comprising both a carrier described hereinabove and at least one hair coloring agent described hereinabove.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Example 1

Preparation of Iron Tannate Hair Coloring Agent

Fifty (50) grams of tannic acid (Mallinckrodt, Catalog No. 1764) dissolved in 100 mL of water were mixed with 5 grams of ferric ammonium citrate (Sigma, Catalog No. F-5879) dissolved in 35 mL of water. The mixture was stirred at room temperature for 24 hours, and then purified.

The reaction mixture was purified by being loaded onto a Sephadex-G-25M column (Ø30×140 mm), pre-washed with 300 mL of water. 150-mL fractions were collected by eluting with water. After elution of the first five fractions containing a polymeric substance of saturated black color, the eluted fractions became almost colorless, implying exhaustive separation. The collected fractions did not give a positive test for unbound ferric (iron III) ions (see description hereinbelow). The water was evaporated by freeze-drying, providing a black powder as product I.

Alternatively, the reaction mixture was purified using ultrafiltration. The mixture was diluted with an, equal volume of water and loaded into a Gyrosep 300 stirring cell (Intersep, UK) supplied with a 10K Omega polyethersulfone membrane (76-mm diameter, Pall, USA), and filtered while stirring under nitrogen at a pressure of 3.8 bar. When the volume of the reaction mixture decreased by half, an equal volume of water was added and the filtration was then repeated. After 6 repetitions, the mixture was diluted again with an equal volume of water, drawn out the stirring cell, and filtered through a paper filter (No 1, Whatman, UK) under reduced pressure. The collected fractions did not give a positive test for free ferric (iron III) ions (see description hereinbelow). The water was evaporated by freeze-drying, providing a black powder as product I.

The above preparations resulted in a polymeric iron-tannate with two notable properties: absence of unbound iron ions and water-solubility.

The purification by either ultrafiltration or gel exclusion chromatography removed unbound iron ions. As discussed hereinabove, residual iron ions may cause destructive oxidation of biopolymers such as keratin, and lead to toxic effects such as corrosive burns and dermatitis.

The above preparations resulted in a water-soluble product, as is suitable for a homogeneous hair colorant composition that is removable by washing. It is therefore unnecessary to add ingredients (e.g. "binders") whose function is to solubilize the iron-tannate in water.

Unbound Iron(III) Test:

10-µL aliquots of each sample were diluted with 30 µL of double-distilled water (DDW), and 10-µL aliquots of 10% potassium ferrocyanide solution was added. The appearance of a characteristic blue coloring indicates the presence of unbound ferric (iron III) ions, whereas the lack of a blue coloring indicates the absence of unbound ferric ions.

Purification by Sephadex G-25M column eliminated the presence of unbound ferric ions, found in non-purified solutions of tannic acid to which iron salts have been added, as shown in Table 1.

TABLE 1

| Exp. No. | Tannic acid | Iron salt | Reaction color after 24 h | Test with $K_4Fe(CN)_6$ after 24 h | Test with $K_4Fe(CN)_6$ after 48 h |
|---|---|---|---|---|---|
| 1 | 30 mg in 60 µL of DDW | 1.8 mg (5.5 µmol) ferric ammonium citrate in 12 µL of DDW | Violet-black | + | + |
| 2 | 30 mg in 60 µL of DDW | 1.5 mg (5.5 µmol) ferrous sulfate heptahydrate in 10 µL of DDW | Green-black | + | + |
| 3 | 30 mg in 60 µL of DDW | 0.9 mg (5.5 µmol) ferric chloride in 12 µL of DDW | Greenish-brown-black | + | + |
| 4 | | 32 mg of product purified with Sephadex G-25M | Violet-black | − | − |

Example 2

Preparation of Melanoidin Condensation Polymer

Thirty (30) grams of L-glycine (Sigma, Catalog No. 7126) and 30 grams of D-glucose (J. T. Baker, Catalog No. 0114) were dissolved together in 110 mL of water, and the obtained solution was evaporated under reduced pressure. The residue was heated at 125° C. for 2.5 hours, during which the white mass became brown, with some foaming. The cooled reaction mixture was re-dissolved in water (180 mL), and 50 mL portions of the solution were purified on Sephadex-S25W columns (Ø30×180 mm), each pre-washed with 330 mL of water. The fractions eluted from each column with 110 mL of water were collected, combined, and evaporated, providing bright brown powder as product II.

Example 3

Preparation of Two-Dye Hair Coloring Compositions

Aqueous stock solutions of products I and II were prepared, each at a concentrations of 0.05 gram/mL. Mixed solutions were prepared by blending the stock solutions in volume ratios of 1:4, 1:2, 1:1, 2:1, and 4:1.

Tresses of yak hair were dyed with the mixed solutions for 1 minute intervals, then blotted with paper and dried with a hair dryer. The tresses were darker than their original color, with shades varying from red-brown to black from mix to mix (see, Table 2).

The color of the dyed hair was partially lost after the hair was rinsed with water, and completely lost after the hair was shampooed.

TABLE 2

| No. | Treatment dye mixture I/II | Visual color |
|---|---|---|
| 1 | 1:4 | Red-brown |
| 2 | 1:2 | Reddish-brown |
| 3 | 1:1 | Brown |
| 4 | 2:1 | Brownish-black |
| 5 | 4:1 | Black |

Thus, a weight ratio of the purified iron-tannate polymer and melanoidin described hereinabove which ranges from 1 part purified iron-tannate polymer to 10 parts melanoidin to 1 part purified iron-tannate polymer to 3 parts melanoidin can color hair a red-brown color.

A weight ratio of the purified iron-tannate polymer and melanoidin described hereinabove which ranges from 1 part purified iron-tannate polymer to 3 parts melanoidin to 1 part purified iron-tannate polymer to 1.5 parts melanoidin can color hair a reddish brown color.

A weight ratio of purified iron-tannate polymer and melanoidin which ranges from 1.5 parts part purified iron-tannate polymer to 1 part melanoidin to 1 part purified iron-tannate polymer to 1.5 parts melanoidin can color hair a brown color.

A weight ratio of purified iron-tannate polymer and melanoidin which ranges from 1.5 parts part purified iron-tannate polymer to 1 part melanoidin to 3 parts purified iron-tannate polymer to 1 part melanoidin can color hair a brownish black color.

A weight ratio of purified iron-tannate polymer and melanoidin which ranges from 3 parts part purified iron-tannate polymer to 1 part melanoidin to 10 parts purified iron-tannate polymer to 1 part melanoidin can color hair a black color.

Example 4

Preparation of Disiloxane-Based Quick-Drying Formulation

An alcohol-free, quick-drying liquid emulsion cosmetic aerosol carrier was prepared having the following formulation:

| | Ingredient | Weight Percents |
|---|---|---|
| | Disiloxane (0.65 CST-Volatile) | 40.00 |
| | Propylene Glycol | 5.00 |
| | Oleth-20 | 2.50 |
| | Simulgel-50 | 5.40 |
| | Simulgel FL | 0.10 |
| | PVP | 0.50 |
| | Water | completing to 100 |
| Preservative: | Sodium Methylparaben | 0.25 |
| Fragrance: | Rose Water | 0.10 |

Dimethyl ether was added to the carrier at a concentration of 35 weight percents of the composition.

Example 5

Preparation of Cyclomethicone-Based Quick-Drying Formulation

An alcohol-free, quick-drying liquid emulsion cosmetic aerosol carrier was prepared having the following formulation:

| | Ingredient | Weight Percents |
|---|---|---|
| | Cyclomethicone | 35.00 |
| | PEG-400 | 5.00 |
| | Simulgel-50 | 1.00 |
| | Simulgel FL | 1.00 |
| | PVP/VA | 1.50 |
| | Phenonip | 0.60 |
| | Ceteth-20 | 3.00 |
| | Water | completing to 100 |
| Preservative: | Phenoxyethanol | 0.20 |

Propane/butane was added to the carrier at a concentration of 30 weight percents of the composition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:
1. A hair-coloring applicator particularly useful for touching-up hair along a hairline of a subject, the applicator comprising:
a quantity of hair-coloring composition;
a container within which said quantity of a hair-coloring composition is stored, said container including an outlet at one end of said container through which said hair-coloring composition is dispensed as a mist;

an attachment attached to said one end of said container; and a shield projecting outwardly from said one end of the container including said outlet;

wherein:
i. one side of said attachment is formed with a slanted top wall terminating in a top rim formed with a projection for receiving said shield; and
ii. said shield includes a plurality of closely spaced teeth having inner surfaces to be pressed against the subject's scalp with the root regions of the hairs passing through the spaces between said teeth and outer surfaces to be exposed to the hair-coloring composition dispensed as a mist from the container, such that the mist-dispensed hair-coloring composition coats the root regions of the hairs passing through the spaces between said teeth while said teeth substantially block the hair-coloring composition from reaching the individual's scalp.

2. The applicator of claim 1, wherein said shield is carried by an attachment attached to the end of the container including said outlet.

3. The applicator of claim 2, wherein said outlet in the container is a nozzle for dispensing said hair-coloring composition in the form of a hair-coloring spray, and said attachment includes an opening aligned with said nozzle.

4. The applicator of claim 3, wherein said attachment further includes a push button controlling the dispensing of the hair-coloring composition via said nozzle, and the opening in said attachment aligned with said nozzle is located between said shield and said push button.

5. The applicator of claim 1, wherein said spaced teeth of the shield are parallel to the longitudinal axis of said container.

6. The applicator of claim 1, wherein said plurality of spaced teeth are arrayed in a generally linear array substantially parallel to, but laterally spaced from, the longitudinal axis of said container.

7. The applicator of claim 1, wherein said teeth are less than 2 mm in width, thickness and spacing.

8. A hair-coloring applicator particularly useful for touching-up hair along a hairline of a subject, the applicator comprising:

a quantity of hair-coloring composition;

a container within which said quantity of a hair-coloring composition is stored, said container including an outlet at one end of the container through which said hair-coloring composition is dispensed as a mist; and an attachment attached to the end of the container carrying said outlet, said attachment including a shield, said attachment being formed with a slanted top wall terminating in a top rim formed with a projection for receiving said shield, said shield having a plurality of spaced parallel teeth which pass between the subject's hair to expose the hair root regions passing through the spaced teeth, while the spaced teeth substantially block the mist-dispensed hair-coloring composition from passing through to the subject's scalp.

9. The applicator of claim 8, wherein said outlet in the container is a nozzle for dispensing said hair-coloring composition in the form of a hair-coloring spray, and said attachment includes an opening aligned with said nozzle, and a push button controlling the dispensing of the hair-coloring spray via said nozzle.

10. The applicator of claim 9, wherein said push button and said opening in the attachment are located on a surface of said attachment which slants towards said shield.

11. The applicator of claim 8, wherein said spaced teeth are generally parallel to the longitudinal axis of said container.

12. The applicator of claim 8, wherein said spaced teeth are arrayed in a generally linear array substantially parallel to, but laterally spaced from, the longitudinal axis of said container.

13. The applicator of claim 8, wherein said teeth are less than 2.0 mm in width, thickness and spacing.

14. The applicator of claim 8, wherein said applicator further comprises an outer housing enclosing said container and serving as a handle for gripping and manipulating the applicator.

15. A method of touching up hair roots of an individual, the method comprising:

a) providing a container within which a quantity of a hair-coloring composition is stored, an attachment attached to said one end of said container and a shield formed of a plurality of closely spaced teeth, the attachment being formed with a slanted top wall terminating in a top rim formed with a projection for receiving said shield, the shield including an inner side facing in one direction and an outer side facing in the opposite direction; and b) when the inner side of the shield is oriented towards and pressed against the individual's scalp so that root regions of hairs to be touched-up are received in the spaces between the teeth, spraying said hair coloring composition from said container over the outer side of the shield to produce a mist over the outer side such that:
i) the hair coloring composition colors the root regions of the hairs passing through the spaces between the teeth, while
ii) the closely-spaced teeth of the shield blocks passage of the hair coloring composition from the outer side to the scalp via the inner side of shield.

16. The method of claim 15 wherein the hair-coloring composition is a quick drying composition.

17. The method of claim 15 wherein the hair coloring spray composition includes a temporary colorant.

18. The system of claim 15 wherein the hair coloring spray composition is a coating composition configured to coat hair.

19. The method of claim 15 wherein the hair coloring spray composition does not flow within teeth of the shield.

20. The method of claim 15 wherein the teeth include bases and tips to define base and tip ends of the shield, and the sprayed hair coloring composition passes within the ambient environment and over the outer side of the shield from the base end of the shield towards the tip end of the shield.

21. The method of claim 15 wherein the teeth include bases and tips to define a longitudinal direction of the shield, and the sprayed hair coloring composition enters the ambient environment in a direction that is primarily oriented along the longitudinal direction of the shield.

22. The method of claim 15, wherein said teeth are less than 2.0 mm in width, thickness and spacing.

23. The method of claim 15, wherein said spaced teeth are generally parallel to the longitudinal axis of said container.

24. The applicator of claim 15, wherein said spaced teeth are arrayed in a generally linear array substantially parallel to, but laterally spaced from, the longitudinal axis of said container.

* * * * *